(12) United States Patent
Dehmer et al.

(10) Patent No.: US 9,134,335 B2
(45) Date of Patent: Sep. 15, 2015

(54) CERAMIC INJECTION NEEDLE

(75) Inventors: Bernhard Dehmer, Rastatt (DE); Joachim-Richard Wagner, Ettlingen (DE)

(73) Assignee: Agilent Technologies, Inc., Santa Clara, CA (US)

( * ) Notice: Subject to any disclaimer, the term of this patent is extended or adjusted under 35 U.S.C. 154(b) by 276 days.

(21) Appl. No.: 13/308,468

(22) Filed: Nov. 30, 2011

(65) Prior Publication Data

US 2012/0164026 A1    Jun. 28, 2012

(30) Foreign Application Priority Data

Dec. 22, 2010  (GB) .................................. 1021702.4

(51) Int. Cl.
| | |
|---|---|
| *B01L 3/02* | (2006.01) |
| *G01N 35/10* | (2006.01) |
| *G01N 30/88* | (2006.01) |
| G01N 30/16 | (2006.01) |
| G01N 30/24 | (2006.01) |

(52) U.S. Cl.
CPC ............ *G01N 35/1081* (2013.01); *B01L 3/021* (2013.01); *G01N 30/88* (2013.01); *B01L 2200/025* (2013.01); *B01L 2200/0689* (2013.01); *B01L 2300/0838* (2013.01); *B01L 2300/12* (2013.01); *G01N 30/16* (2013.01); *G01N 30/24* (2013.01); *G01N 2030/8804* (2013.01); *Y10T 29/49826* (2015.01)

(58) Field of Classification Search
USPC ......... 422/501, 511–512, 524, 922, 931, 525, 422/546; 73/863.32, 864, 864.01, 864.14, 73/864.15, 864.21, 864.74, 864.87; 604/21, 187–188, 540, 322
See application file for complete search history.

(56) References Cited

U.S. PATENT DOCUMENTS

| | | | |
|---|---|---|---|
| 3,901,413 A | 8/1975 | Harris, Sr. | |
| 4,226,119 A | 10/1980 | Buser | |
| 5,194,226 A * | 3/1993 | Tomoff et al. | ................. 422/509 |
| 5,525,298 A * | 6/1996 | Anami | .............................. 422/63 |
| 5,525,303 A * | 6/1996 | Ford et al. | ...................... 422/535 |
| 5,730,943 A * | 3/1998 | Ford et al. | ...................... 422/535 |
| 6,531,097 B1 * | 3/2003 | Vojnovic et al. | ............ 422/82.07 |

(Continued)

FOREIGN PATENT DOCUMENTS

| | | |
|---|---|---|
| EP | 1795264 A1 | 6/2007 |
| WO | 2007026742 A1 | 3/2007 |
| WO | WO2010026742 | 3/2010 |

OTHER PUBLICATIONS

Search Report issued Apr. 26, 2011, by the United Kingdom Intellectual Property Office with regard to related Application No. GB1021702.4 (4 pages).

(Continued)

*Primary Examiner* — Brian R Gordon

(57) ABSTRACT

A needle for handling a fluid in an analysis system is described. The needle includes a needle body made of a ceramic material and having a fluid conduit extending between a fitting end and a seat end. The fitting end is configured to be connected to a fitting and the seat end (308) being insertable into a seat. The needle body is tapering towards the fitting end. A fixing body is arranged on the needle body next to the fitting end for exerting an axial force when the needle body is connected to the fitting, and a slide-on element to be slid over the needle body so as to push the fixing body towards the fitting end.

21 Claims, 5 Drawing Sheets

(56) References Cited

U.S. PATENT DOCUMENTS

| | | | |
|---|---|---|---|
| 6,793,632 B2* | 9/2004 | Sohrab | 600/573 |
| 7,144,554 B1* | 12/2006 | Gulla et al. | 422/521 |
| 8,221,358 B2* | 7/2012 | McKay | 604/187 |
| 8,414,560 B2* | 4/2013 | Bush et al. | 604/535 |
| 8,758,587 B2* | 6/2014 | Sugiyama et al. | 204/451 |
| 2002/0026821 A1* | 3/2002 | Zimmermann et al. | 73/23.35 |
| 2004/0126279 A1* | 7/2004 | Renzi et al. | 422/100 |
| 2004/0236250 A1* | 11/2004 | Hodges et al. | 600/583 |
| 2006/0239863 A1* | 10/2006 | Zach et al. | 422/100 |
| 2007/0282265 A1 | 12/2007 | Shigematsu et al. | |
| 2008/0038152 A1 | 2/2008 | Van Pelt | |
| 2008/0269697 A1* | 10/2008 | Bush et al. | 604/263 |
| 2008/0309076 A1* | 12/2008 | Cormier | 285/256 |
| 2009/0075321 A1* | 3/2009 | Obeid et al. | 435/29 |
| 2009/0078322 A1* | 3/2009 | Thomas et al. | 137/15.09 |
| 2009/0295156 A1* | 12/2009 | Ford et al. | 285/384 |
| 2010/0224546 A1* | 9/2010 | Ellis et al. | 210/232 |
| 2010/0318061 A1* | 12/2010 | Derrick et al. | 604/508 |
| 2012/0024417 A1* | 2/2012 | Voit et al. | 141/1 |
| 2012/0160754 A1* | 6/2012 | Falk-Jordan | 210/198.2 |
| 2014/0103065 A1* | 4/2014 | Lambrecht et al. | 222/81 |

OTHER PUBLICATIONS

Notification of Registration and Decision to Grant mailed Nov. 30, 2012 in Chinese Application No. 201120578850.1.

Machine Translation of Office Action mailed Jun. 11, 2012 in Chinese Application No. 201120578850.1.

Machine Translation of Office Action mailed Sep. 13, 2012 in Chinese Application No. 201120578850.1.

* cited by examiner

CERAMIC INJECTION NEEDLE

CROSS REFERENCE TO RELATED APPLICATIONS

This claims priority of a British Application No. GB1021702.4, filed on Dec. 22, 2010, the disclosure of which is incorporated by reference in its entirety.

BACKGROUND ART

The present invention relates to a needle for an analysis system.

In liquid chromatography, a fluidic sample and an eluent (liquid mobile phase) may be pumped through conduits and a column in which separation of sample components takes place. In a sample loop, the sample may be injected into a fluidic path by a mechanically drivable needle. The drivable needle is controllable to be moved out of a seat of the sample loop into a vial to receive a fluid and back from the vial into the seat. The column may comprise a material which is capable of separating different components of the fluidic analyte. Such a material, so-called beads which may comprise silica gel, may be filled into a column tube which may be connected downstream to other components, such as a detector, a fractioner, a waste, etc., by conduits.

Known analysis systems may handle fluidic samples, buffers, and rinsing fluids using hollow needles in which a fluid may be sucked for transport to a destination. When handling multiple fluids with such a needle, contamination of the needle may occur and impurities may be introduced in containers holding such fluids or in other components of the analysis system. Such an undesired contamination or carryover may be overcome by using a ceramic needle.

US 2007/0282265 discloses a non tissue-destructive hollow needle not damaging the tissue of a needle inserting portion and an indwelling needle using the hollow needle. A hollow needle is made from ceramic, has an outer diameter of 1-5 mm, and a wall thickness of 0.6-1.8 mm, and gives less damage to the tissue of a needle inserting portion. Worth noting is that the ceramic is zirconium and its oxide. The non tissue-destructive hollow needle can be used as a indwelling needle. The indwelling needle is constructed by inserting a resin straight fine needle, with chemical resistant and corrosion resistant properties, into the ceramic hollow needle, inserting the hollow needle, installed on the straight fine needle, into a hollow needle outer tube, and providing a connection tube, configured for connection to an external extension tube, on the hollow needle outer tube. The connection tube is connected to the external extension tube through a connection ring. A fluorocarbon resin is suitably used as the chemical resistant, corrosion resistant resin.

EP 1,795,264 discloses a needle for handling a fluid in an analysis system, the needle comprising a needle body having a fluid conduit, and having a fluid repellant surface portion.

However, conventional ceramic needles may still be problematic due to their brittle character and due to challenges connected with the mounting of such a needle particularly in view of sealing issues in high pressure applications.

DISCLOSURE

It is an object of the invention to provide a needle being mountable to a fitting in an efficient manner. The object is solved by the independent claims. Further embodiments are shown by the dependent claims.

According to an exemplary embodiment of the present invention, a needle for handling a fluid in an analysis system is provided, the needle comprising a needle body made of a ceramic material and having a fluid conduit (such as a cylindrical lumen) extending between a fitting end and a seat end, the fitting end being connectable to a fitting and the seat end being insertable into a seat, wherein the needle body is tapering (i.e. narrowing gradually or stepwise towards a point or narrow portion, in the context of this application), particularly conically tapering (i.e. narrowing in accordance with a cone-shape, in the context of this application), towards the fitting end, a fixing body arranged on the needle body next to (or at) the fitting end for exerting an axial force (particularly a force along a directions which corresponds to a linear extension of the needle body or its fluid conduit) when the needle body is connected to the fitting, and a slide-on element to be slid over the needle body so as to push the fixing body towards the fitting end (particularly when the slide-on element is mounted on a fitting).

According to another exemplary embodiment, an analysis system for analyzing a fluid is provided, the analysis system comprising a needle having the above-mentioned features.

According to yet another exemplary embodiment, a method of manufacturing a needle for handling a fluid in an analysis system is provided, wherein the method comprises providing a needle body of a ceramic material and having a fluid conduit extending between a fitting end and a seat end, the fitting end being connectable to a fitting and the seat end being insertable into a seat, wherein the needle body is tapering, particularly conically tapering, towards the fitting end, arranging a fixing body on the needle body next to the fitting end for exerting an axial force when the needle body is connected to the fitting, and sliding a slide-on element over the needle body so as to push the fixing body towards the fitting end.

According to an exemplary embodiment of the invention, a needle for a fluidic analysis system is provided, which combines a plurality of advantages due to its combination of a ceramic needle body, a fixing body fixedly arranged on the needle body close to a fitting end, and an element to be slid on the needle body for exerting a pressing force onto the fixing body and hence onto the needle body when being inserted into a fitting to provide for a fluid-tight coupling between fluid conduits of needle body and fitting. A ceramic needle body is particularly appropriate for analysis systems such as liquid chromatography apparatuses, since many fluidic samples including biological samples (which may have proteins or genes) will not or only to a very small amount adhere on ceramic material, thereby ensuring small or no carryover. On the other hand, a ceramic material can be quite brittle. At the same time, a ceramic needle body usually needs to be quite long because it has to be immersed into solutions such as a fluidic sample stored in a relatively large vial. Such a brittle needle has to be connected to a fitting in a fluid-tight manner even under high pressure conditions up to 600 bar or more (for instance 1200 bar). Such a fluid-tight connection of a brittle ceramic body with a fitting can be achieved by a combination of the fixing body and the slide-on element. Ceramic material alone would be difficult to be clamped to surrounding material of the fitting, so that this function is provided by a correspondingly designed component, i.e. the fixing body which may therefore be made of another material than the needle body. To apply a pressing force from a backward position onto the fixing body to thereby push the fixing body and hence the needle body against the fitting, the slide-on element is provided which may be secured to the fitting to maintain its pushing force. Thus, the combination of the integrally formed needle body/fixing body member on the one hand, and the slidable slide-on element on the other hand provides a very simple system which can be handled easily by a user. It can be easily operated to obtain a reliable high pressure sealing while at the same reducing carryover and preventing excessive mechanical forces acting on the brittle ceramic needle body. By providing a tapering end at the needle body which is to be to fitted with the fitting, a sort of centering mechanism is provided, which acts as an assembly guidance and at the same time contributes to the sealing function.

In the following, further exemplary embodiments of the needle will be explained. However, these embodiments also apply to the analysis system and the method.

In an embodiment, the fixing body is fixedly (for instance inseparably) mounted on the needle body. Hence, fixing body and needle body may be firmly connected to one another. The rigid connection between the fixing body and the needle body may be realized by soldering, adhering, welding or the like. Thus, a fluid-tight (particularly liquid-tight) connection between the fixing body and the needle body may be provided. Furthermore, by rigidly connecting fixing body and needle body, only a very small number of members has to be handled by a user.

In an embodiment, the fixing body is tapering, particularly conically tapering, towards the tapering, particularly conically tapering, of the needle body. Hence, two for instance conically tapering elements may be fixedly connected to one another. In an embodiment, the tapering between the fixing body and the needle body may be stepwise. Alternatively, needle body and fixing body may taper continuously.

In an embodiment, the fixing body is made of a ductile material, and the needle body is made of a non-ductile material. Ductility is a mechanical property that describes the extent to which solid materials can be plastically deformed without fracture. In an embodiment, the fixing body is made of a material that will permit plastic deformation without fracturing, hence having the ability to adopt its shape without breaking. In contrast to this, the needle body may be made of a non-ductile or brittle material, which will break before any technically significant deformation. Thus, the needle body may provide a mechanical robustness, whereas the fixing body may allow to be deformed when mounted in the fitting, thereby enabling a clamping with the fitting.

In an embodiment, the fixing body is made of a material being deformable (particularly plastically deformable) under pressure, particularly is made of a metal or plastic. For example, the fixing body may be made of steel, iron, copper or aluminum. It may also be made of a plastic material such as polyetheretherketone (PEEK).

In an embodiment, the slide-on element has a tubular shape with an inner lumen, bore or recess for receiving and enclosing circumferentially the needle body. The slide-on element may be equipped with a fitting fastener, particularly an external thread, for cooperation with a needle body fastener, particularly an internal thread, of a reception of the fitting. Upon inserting the integrally formed member constituted by fixing body and needle body into a reception of the fitting, the connection of the integrally formed body with the fitting is performed by sliding the slide-on element from a rear position over the needle body followed by a connection between the slide-on element and the fitting by engaging fitting fastener and needle body fastener. For instance, corresponding threads may be provided at the reception of the fitting and at the outer surface of the slide-on element as the fasteners. This results in an easy to handle and reliable screwing connection being compatible with a high pressing force. However, many other kinds of connections are possible such as a locking connection, a snap-in connection, a bayonet connection, a magnetic connection or the like.

In an embodiment, the ceramic needle body is made of aluminum oxide, zirconium oxide or yttrium-stabilized zirconium oxide. The provision of yttrium may render the ceramic material slightly flexible, wherein the yttrium additive may be supplied to the ceramic material during a sintering procedure. Thus, the risk of breakage of the brittle needle during operation can be reduced. The mentioned ceramic materials have proper surface adhesion properties, which can reduce or eliminate carry-over when handling fluidic samples, such as biological samples.

In an embodiment, the needle body is made of a single material. This guarantees a cost efficient manufacture of the needle body and a constantly high mechanical robustness over the entire extension of the needle body.

In an embodiment, a cone angle of the conically tapering of the needle body is smaller than a cone angle of the conically tapering of the fitting so that a pressure-tight sealing is formed between the conically tapering of the needle body and the conically tapering of the fitting. The "cone angle" may be the angle at the tip of the cone approached and enclosed by the lateral surface of the conically tapering part. The needle body may be more spiky close to the fitting end as compared to the fitting reception which may ensure a proper sealing, when the needle body is inserted into the fitting.

Also towards the seat end, the needle body may be tapering, particularly conically tapering. This on the one hand ensures that the needle body is properly insertable into the seat, wherein the conically tapering and a corresponding conically tapering reception of the seat may provide for some kind of centering or insertion guidance. On the other hand, the needle body may be movable out of the seat and may be insertable into a fluid container such as a vial and for this reason may have to, in some embodiments, penetrate a membrane closing the vial. This membrane may be traversed by a tapering tip of the needle body at the seat end. The tapering towards the fitting end may be less steep so that a reduction of the diameter per length unit of the needle body is larger at the fitting end as compared to the seat end. For both ends of the needle body as well as for the corresponding portions of the fitting and the seat, a conical tapering characteristic may be preferred, since this contributes to a sealed connection of the respective connected two elements. However, any other kinds of tapering may also be possible, for instance a step-like tapering or a tapering having a certain curvature such as a convex or a concave tapering. Between the tapering portions of the needle body on the opposing ends, a cylindrical portion of the needle body may be located.

In an embodiment, the needle body has a length in a range between about 1 cm and about 10 cm, particularly in a range between about 3 cm and about 7 cm. With a length of for instance 5 cm, the needle body is appropriate to be used in a sample injector of a liquid chromatography apparatus in which the needle has to move between a needle seat and a fluid container such as a vial. With such relatively large lengths of the needle body, the mechanically robust character of the ceramic material is of particular advantage.

In an embodiment, the fluid conduit has a diameter in a range between about 0.01 mm and about 0.5 mm, particularly in a range between about 0.05 mm and about 0.2 mm. Particularly in combination with a relatively long extension of the needle body, it can be seen that the diameter of the fluid conduit is very small, for instance in the order of magnitude of 0.1 mm. With these small diameters which are advantageous for microfluidic and particularly nanofluidic applications, there is conventionally the problem of a high carryover of samples, which could adhere to the wall of the needle body. By providing a needle body consisting of ceramic material, these small diameters are possible without the risk of a carryover, at the same time providing for a high robustness of the needle. By manufacturing the fitting body from another material than the needle body, any problems of a pure ceramic connection for combined clamping and sealing purposes can be overcome by embodiments of the invention, thereby at the same time allowing to make full use of the ceramic material of the needle body.

In an embodiment, the needle comprises a spring-loading element arranged between the fixing body and the slide-on element. In an embodiment, the spring-loading element is a disk spring. By sandwiching such a spring loading element between the fitting body and the slide-on element, it is possible that changes of the fastening characteristics (such as the pushing force provided by slide-on element to fitting body) over time may be compensated. If, for instance due to a small readjustment of the arrangement of the various components relative to one another over a long period of time, the sealing performance between fitting and needle becomes deteriorated, a biased spring loading element sandwiched between fixing body and slide-on element may compensate for such changes and may ensure to continuously apply a pushing force of the fitting body towards the fitting. A disk spring is an advantageous example for the spring-loading element, because it is small in size and provides for an axial biasing force. However, other springs are possible such as a helical spring.

In an embodiment, the needle comprises the fitting being connected or being configured for being connectable to the fitting end of the needle body. Correspondingly, the geometry and dimensions of fitting on the one hand and needle body on the other hand may be adjusted to one another so as to allow for a sealed connection. Such a seal connection may be such that it still provides a liquid-tight sealing performance if the pressure exceeds 600 bar, particularly exceeds 1200 bar.

In an embodiment, the fitting has a reception (or an accommodation space) for receiving at least parts of the needle body, the fixing body and/or the slide-on element, the reception being tapering, particularly conically tapering, in accordance with the tapering, particularly conically tapering, of the needle body. Such a reception, recess or accommodation space of the fitting may be conically tapering in a way which corresponds to the conically tapering of the needle body. However, the conically tapering of both sections does not necessarily have to be the same but may intentionally differ in steepness which may improve the sealing characteristic.

In an embodiment, the fitting has a fluid conduit in fluid communication with the fluid conduit of the needle body when at least parts of the needle body, the fixing body and the slide-on element are mounted in the reception of the fitting. By taking this measure, a continuous fluid communication from the seat end of the needle body towards the fitting end of the needle body and from there to the fitting may be enabled, and this even for high pressure applications and low volume or pumping rate applications.

In the following, further exemplary embodiments of the analysis system will be explained. However, these embodiments also apply to the needle and the method.

In an embodiment, the analysis system comprises the seat, wherein the needle is selectively insertable into the seat or is movable out of the seat. In such an embodiment, needle and seat may form a needle-seat arrangement of a sample injector, particularly for a liquid chromatography apparatus.

In an embodiment, the seat (more precisely its engagement portion being engaged by the seat end of the needle) is radially elastic, e.g. made of SST (stainless steel) with high proof strength, so that the seat snugly adjusts to the seat end of the needle upon being inserted into the seat. Such an embodiment is highly advantageous when using a ceramic material for the needle body being very brittle, i.e. non-ductile. Ceramic materials are able to withstand for high compression load but break on low tensile load. In this design the load distribution while sealing the needle to the seat is arranged to be mainly a compression load for the ceramic needle and a tensile load for the engaged part of the metal seat. Even in case of a misalignment between the needle and the seat and/or profile defects along the contact area of needle and seat, there is low risk that the ceramic needle body breaks due to the corresponding mechanical forces as long the superposition of forces are manly compression forces within the ceramic needle.

Still referring to the previously described embodiment, the seat may comprise a sheath section (or a sleeve section) providing the radially elastic property. Such a sheath section may be a thin-walled structure which can be elastically deformed upon the exertion of a force by the needle. More particularly, such a sheath section may be a conical sheath section, i.e. may be basically shaped like a hollow cone with a thin wall. The function of the device is particularly supported by the conical geometry, since this will result in an appropriate force direction.

It is preferred that the sheath section is made of a metal or any other sufficiently hard material, so that a ceramic-metal material combination of needle and seat is provided to fulfil the adjustment task. More particularly, such a metal may be steel, particularly hardened steel. In contrast to conventional approaches, a sealing annulus (i.e. a ring along which the sealing occurs) between needle and seat is therefore not formed by a soft/hard material combination, but by a hard/hard material combination which is considered to increase the lifetime of the apparatus since it is less prone to damage even in case of a misalignment between needle and seat during the insertion procedure.

In order to further increase the lifetime particularly of the seat, an inner surface of the sheath section facing the needle during the insertion of the needle (and hence opposing a seat casing) may be specifically hardened. Such a hardened surface is less prone to failure or damage even when being hit by a misaligned hard ceramic needle.

In an embodiment, the analysis system is configured as at least one of the group consisting of an autosampler device, a fractioner device, a measurement device for performing a measurement in a coupled measurement environment, a measurement device for measuring at least one physical, chemical or biological parameter, a measurement device for performing a measurement of a fluidic sample, a sensor device, a device for chemical, biological and/or pharmaceutical analysis, a fluid separation system configured for separating compounds of a fluid, a test device for testing a device under test or a substance, a capillary electrophoresis device, a liquid chromatography device, a gas chromatography device, an electronic measurement device, and a mass spectroscopy device.

The analysis system may further comprise a pump configured for pumping fluid through the system. The fluid may be sucked from a vial into the needle and from there to a capillary. As a pump, a piston pump, a peristaltic pump, etc., may be implemented.

The analysis system may comprise a sample loop for handling a fluidic sample. Such a sample loop may be part of a liquid chromatography apparatus and may allow to inject a sample into the sample loop via the needle at an end portion of a capillary which can be pivoted from the seat of the sample loop to immerse into a fluid end. After having taken up the fluid, the needle can be moved back into the seat so that the injected fluid can be introduced via the sample loop onto a chromatographic column for fluid separation. Such a fluid separation may then be performed by separately releasing different fractions of a sample trapped on the chromatographic column by running a gradient during which a solvent with varying composition may be conducted through the chromatographic column.

In an embodiment, the analysis system may be configured as an autosampler for injecting a fluidic sample in an apparatus being in fluid communication with the capillary. Such an autosampler may be a device or module which, in an automatic manner, allows to handle fluid in a specific manner, for instance in accordance with a dedicated mechanism of controlling different vials so that a specific sample composition may be adjusted.

In an embodiment, the above mentioned apparatus served by the autosampler may be a chromatographic column. Therefore, the autosampler may take up a sample and may inject the sample towards a chromatographic column for sample separation.

The analysis system may thus include or cooperate with a processing element (such as a chromatographic column) filled with a separating material. Such a separating material which may also be denoted as a stationary phase may be any material which allows an adjustable degree of interaction with a sample so as to be capable of separating different components of such a sample. The separating material may be a liquid chromatography column filling material or packing material comprising at least one of the group consisting of polystyrene, zeolite, polyvinylalcohol, polytetrafluorethylene, glass, polymeric powder, silicon dioxide, and silica gel, or any of above with chemically modified (coated, capped etc) surface. However, any packing material can be used which has material properties allowing an analyte passing through this material to be separated into different components, for instance due to different kinds of interactions or affinities between the packing material and fractions of the analyte.

At least a part of the processing element may be filled with a fluid separating material, wherein the fluid separating material may comprise beads having a size in the range of essentially 1 μm to essentially 50 μm. Thus, these beads may be small particles which may be filled inside the separation section of the microfluidic device. The beads may have pores having a size in the range of essentially 0.01 μm to essentially 0.2 μm. The fluidic sample may be passed through the pores, wherein an interaction may occur between the fluidic sample and the pores.

The analysis system may be configured as a fluid separation system for separating components of the sample. When a mobile phase including a fluidic sample passes through the fluidic device, for instance with a high pressure, the interaction between a filling of the column and the fluidic sample may allow for separating different components of the sample, as performed in a liquid chromatography device.

However, the analysis system may also be configured as a fluid purification system for purifying the fluidic sample. By spatially separating different fractions of the fluidic sample, a multi-component sample may be purified, for instance a protein solution. When a protein solution has been prepared in a biochemical lab, it may still comprise a plurality of components. If, for instance, only a single protein of this multi-component liquid is of interest, the sample may be forced to pass the columns. Due to the different interaction of the different protein fractions with the filling of the column (for instance using a gel electrophoresis device or a liquid chromatography device), the different samples may be distinguished, and one sample or band of material may be selectively isolated as a purified sample.

The analysis system may be configured to analyze at least one physical, chemical and/or biological parameter of at least one component of the mobile phase. The term "physical parameter" may particularly denote a size or a temperature of the fluid. The term "chemical parameter" may particularly denote a concentration of a fraction of the analyte, an affinity parameter, or the like. The term "biological parameter" may particularly denote a concentration of a protein, a gene or the like in a biochemical solution, a biological activity of a component, etc.

The analysis system may be configured to conduct a liquid mobile phase through the processing element and optionally a further processing element. As an alternative to a liquid mobile phase, a gaseous mobile phase or a mobile phase including solid particles may be processed using the fluidic device. Also materials being mixtures of different phases (solid, liquid, gaseous) may be processed using exemplary embodiments. The sample separation device may be configured to conduct the mobile phase through the system with a high pressure, particularly of at least 600 bar, more particularly of at least 1200 bar.

The analysis system may be configured as a microfluidic device. The term "microfluidic device" may particularly denote a fluidic device as described herein which allows to convey fluid through microchannels having a dimension in the order of magnitude of less than 500 μm, particularly less than 200 μm, more particularly less than 100 μm or less than 50 μm or less. The analysis system may also be configured as a nanofluidic device. The term "nanofluidic device" may particularly denote a fluidic device as described herein which allows to convey fluid through nanochannels with a flow rate of less than 100 nl/min, particularly of less than 10 nl/min.

Exemplary embodiments may be implemented in a sample injector module of a liquid chromatography apparatus which sample injector module may take up a sample from a fluid container and may inject such a sample in a conduit for supply to a separation column. During this procedure, the sample may be compressed from, for instance, normal pressure to a higher pressure of, for instance several hundred bars or even 1000 bar and more. An autosampler may automatically inject a sample from the vial into a sample loop. A tip or needle of the autosampler may dip into a fluid container, may suck fluid into the capillary and may then drive back into a seat of a sample loop to then, for instance via a switchable fluidic valve, inject the fluid towards a sample separation section of the liquid chromatography apparatus.

BRIEF DESCRIPTION OF DRAWINGS

Other objects and many of the attendant advantages of embodiments of the present invention will be readily appreciated and become better understood by reference to the following more detailed description of embodiments in connection with the accompanied drawings. Features that are substantially or functionally equal or similar will be referred to by the same reference signs.

Figure 1:
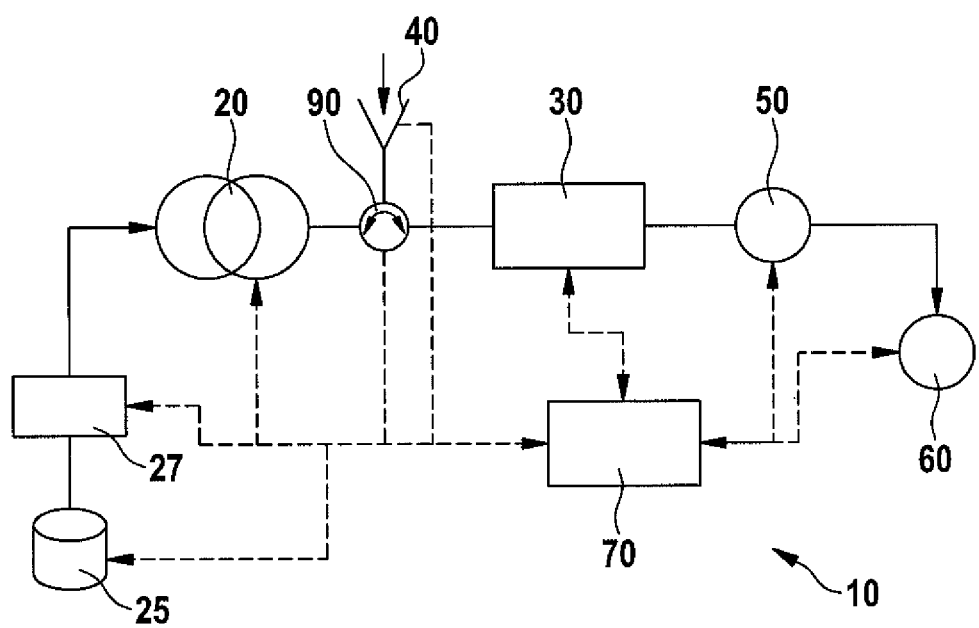
FIG. 1 shows a liquid separation device, in accordance with embodiments of the present invention, e.g. used in high performance liquid chromatography (HPLC).

The illustration in the drawing is schematically.

Referring now in greater detail to the drawings, FIG. 1 depicts a general schematic of a liquid separation system 10. A pump 20 receives a mobile phase from a solvent supply 25, typically via a degasser 27, which degases and thus reduces the amount of dissolved gases in the mobile phase. The pump 20—as a mobile phase drive—drives the mobile phase through a separating device 30 (such as a chromatographic column) comprising a stationary phase. A sampling unit 40 is provided between the pump 20 and the separating device 30 in order to subject or add (often referred to as sample introduction) a sample fluid into the mobile phase. The stationary phase of the separating device 30 is configured for separating compounds of the sample liquid. A detector 50 is provided for detecting separated compounds of the sample fluid. A fractionating unit 60 can be provided for outputting separated compounds of sample fluid.

While the mobile phase can be comprised of one solvent only, it may also be mixed from plural solvents. Such mixing might be a low pressure mixing and provided upstream of the pump 20, so that the pump 20 already receives and pumps the mixed solvents as the mobile phase. Alternatively, the pump 20 might be comprised of plural individual pumping units, with plural of the pumping units each receiving and pumping a different solvent or mixture, so that the mixing of the mobile phase (as received by the separating device 30) occurs at high pressure and downstream of the pump 20 (or as part thereof). The composition (mixture) of the mobile phase may be kept constant over time, the so called isocratic mode, or varied over time, the so called gradient mode.

A data processing unit 70, which can be a conventional PC or workstation, might be coupled (as indicated by the dotted arrows) to one or more of the devices in the liquid separation system 10 in order to receive information and/or control operation. For example, the data processing unit 70 might control operation of the pump 20 (e.g. setting control parameters) and receive therefrom information regarding the actual working conditions (such as output pressure, flow rate, etc. at an outlet of the pump). The data processing unit 70 might also control operation of the solvent supply 25 (e.g. setting the solvent's or solvent mixture to be supplied) and/or the degasser 27 (e.g. setting control parameters such as vacuum level) and might receive therefrom information regarding the actual working conditions (such as solvent composition supplied over time, flow rate, vacuum level, etc.). The data processing unit 70 might further control operation of the sampling unit 40 (e.g. controlling sample injection or synchronization sample injection with operating conditions of the pump 20). The separating device 30 might also be controlled by the data processing unit 70 (e.g. selecting a specific flow path or column, setting operation temperature, etc.), and send—in return—information (e.g. operating conditions) to the data processing unit 70. Accordingly, the detector 50 might be controlled by the data processing unit 70 (e.g. with respect to spectral or wavelength settings, setting time constants, start/stop data acquisition), and send information (e.g. about the detected sample compounds) to the data processing unit 70. The data processing unit 70 might also control operation of the fractionating unit 60 (e.g. in conjunction with data received from the detector 50) and provides data back.

Figure 2:
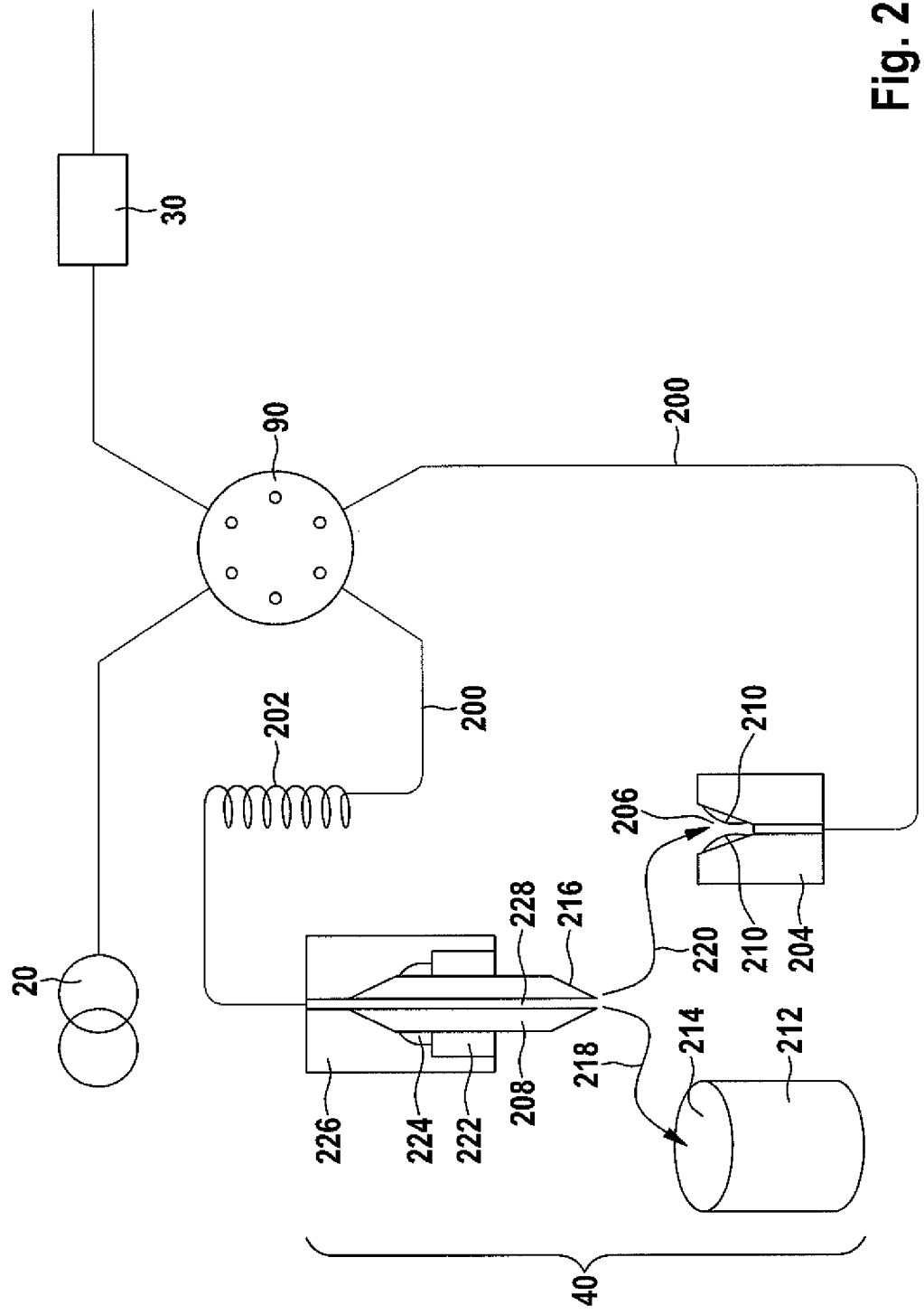
FIG. 2 shows a sample injector of a liquid separation device in accordance with an embodiment of the present invention.

FIG. 2 schematically shows part of a sample injector of the liquid separation system 10 of FIG. 1, particularly shows a more detailed view of part of the sampling unit 40 shown in FIG. 1.

More precisely FIG. 2 shows as to how a sample can be loaded onto the liquid separation system 10, which can then be supplied, by the pumping pressure of the pump 20, towards the chromatographic separation column 30. For this purpose, switchable valve 90 is correspondingly controlled to provide the corresponding fluid parts.

FIG. 2 shows a fluidic conduit 200, which provides for a fluid communication of the various components of FIG. 2. Particularly, it contains a sample loop 202, which can be brought in fluid communication with a seat 204. The seat 204 has a reception 206 for receiving a seat tip of a needle 208. Furthermore, the reception 206 is conically tapering and has one or more elastically deformable structures 210 configured to receiving the ceramic needle 208 in a centering way.

The needle 208 may now selectively be moved between the reception 206 of the seat 204 on the one hand and a vial 212, which may include a fluidic sample to be injected, on the other hand. The vial 212 may be closed by a membrane 214, which can be penetrated by a tapering part of needle tip 216. Two arrows 218, 220 indicate that the needle body 208 can be selectively moved between the vial 212 and the seat 204.

The needle body 208 is connected by a fixing body 224 and a slide-on element 222 to a fitting 226 in a way as will be described below in more detail.

Fluid from the vial 212 may first be injected by sucking it into a fluid conduit 228 within the needle body 208 when the needle body 208 dips into the vial 212, and the fluid may be accommodated in the sample loop 202. After that, the needle body 208 filled with the fluid may be moved from the vial 212 into the reception 206 of the seat 204, so as to inject the fluid into the fluidic conduit 200. Subsequently, by correspondingly switching the switching valve 90, this fluid may then be injected in the fluidic path between the pump 20 and the chromatographic separation column 30.

In the following, referring to FIG. 3, the detailed construction of a needle 300 according to an exemplary embodiment of the invention will be explained.

Figure 3:
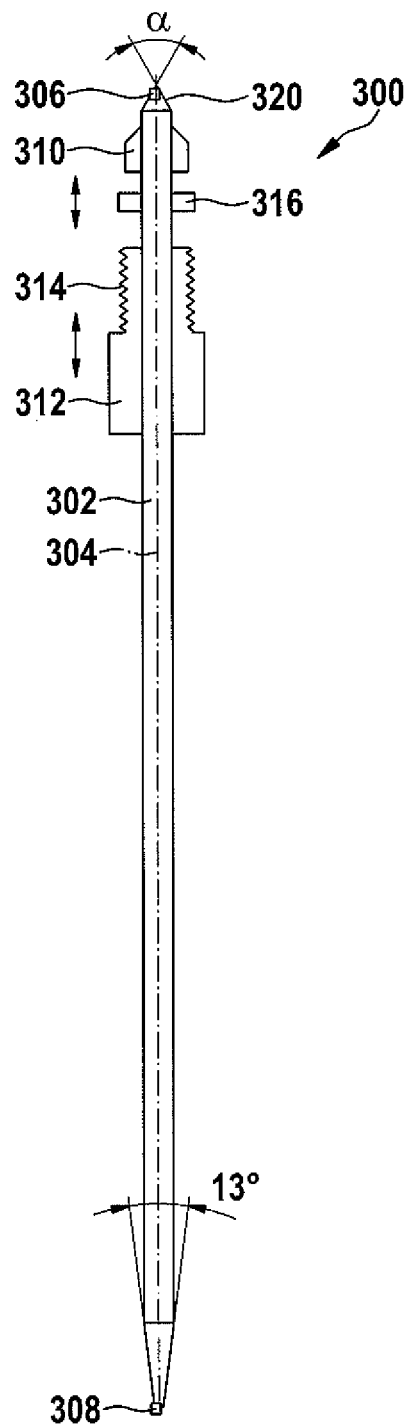
FIG. 3 shows a needle for a sample injector according to an embodiment of the present invention.

FIG. 3 shows a needle 300 for handling a fluidic sample in a liquid chromatography apparatus 10.

The needle 300 comprises a needle body 302 made of a ceramic material, for instance of zirconium oxide as the only material, and has an axially aligned fluid conduit 304 extending linearly between a fitting end 306 and a seat end 308. The fitting end 306 is connectable to a fitting (compare FIG. 4 and FIG. 5). The seat end 308 is insertable into a seat (compare FIG. 6). As can be taken from FIG. 3, the needle body 302 is conically tapering towards the fitting end 306. The conically tapering portion is denoted with reference numeral 320.

Figure 4:
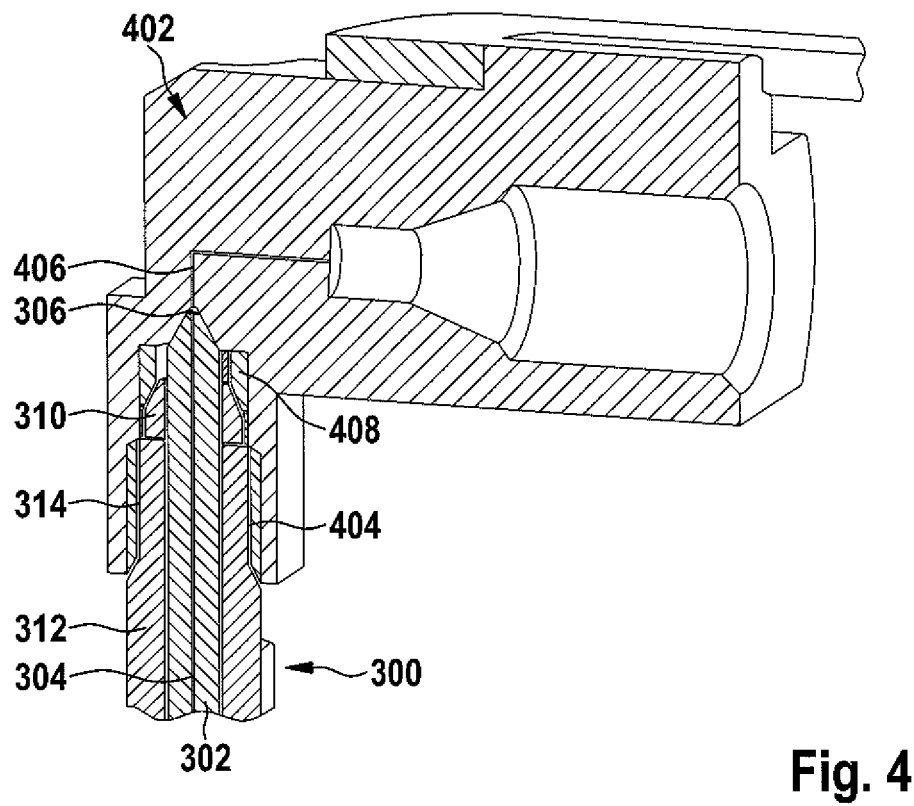
FIG. 4 and FIG. 5 show different views of a needle body mounted in a fitting for a sample injector according to an embodiment of the present invention.
Figure 5:
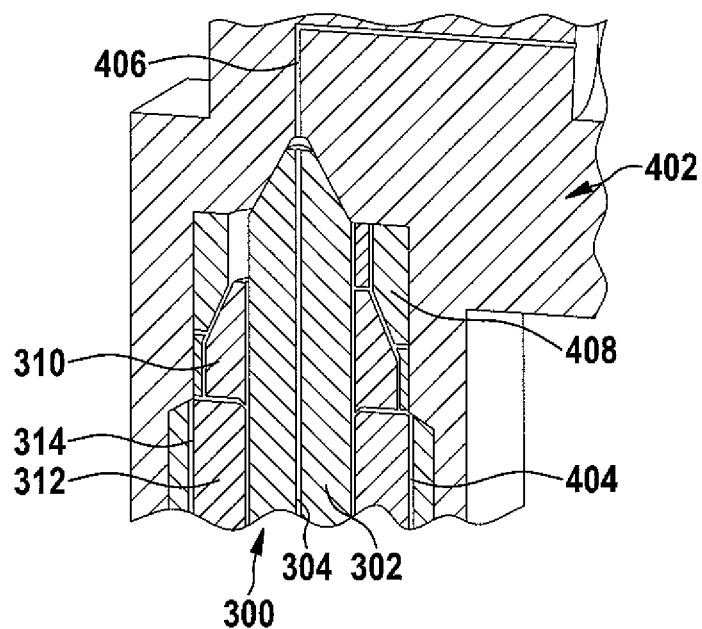

Furthermore, a fixing body 310 is soldered rigidly onto the needle body 302 next to the fitting end 306 and is adapted for exerting an axial force onto the needle body 302, when the needle body 302 is connected to the fitting, as can be shown in FIG. 4 and FIG. 5.

A slide-on element 312 configured as a sleeve with an external threading 314 extending along an actual portion thereof can be slid with some clearance over and along the needle body 302 from a seat end 308. After being slid over the needle 302, the slide-on element 312 pushes the fixing body 310 towards the fixing end 306, when the needle body 302 is mounted in a fitting. As can further be taken from FIG. 3, the fixing body 310 is also conically tapering towards the conically tapering of the needle body 302 so that a double cone is formed. Therefore, the combination of the fitting end 320 of the needle body 302 and the fixing body 310 constitute a form closure connection when be mounted to the fitting and may also provide at their rear position an undercut section, which provides the actuation surface for the slide-on element 312. The fixing body 310 is made of iron or plastic material having a ductile characteristic, whereas the needle body 302 consists of the non-ductile or brittle ceramic material. Hence, the fixing body 310 is plastically deformable upon applying a pressure when screwing the slide-on element 310 having the outer thread 314 onto a corresponding inner thread of a reception of the fitting. Therefore, the fixing body 310 is slightly deformed to provide for a clamping connection with an abutting surface of the reception of the fitting. In contrast to this, the ceramic material of the needle body 302 is not compressed and suppresses carryover or adhesion of sample materials at an interior of the fluid conduit 304 and at the same provides a sufficient mechanical rigidity to allow to withstand the considerable mechanical load occurring in high pressure applications in HPLC.

As can be taken from FIG. 3, the needle body 302 is conically tapering towards the seat end 308. The conical tapering towards the fitting end 306 has a different steepness than the conical tapering towards the seat end 308. As can be taken from FIG. 3, the conical tapering towards the seat end 308 is described by a cone angle of about 13°, whereas the corresponding tapering angle α towards the fitting end 306 is larger, for instance is in a range between 20° and 80°. Thus, cone angle α of the conical tapering at the fitting end 306 of needle body 302 is larger than cone angle (13°) of the conically tapering of the fitting.

In the shown embodiment, the needle body 302 has a length of 5 cm, however, other lengths are of course possible. An inner diameter of the fluid conduit 304 is 0.14 mm in the shown embodiment.

A disk spring 316 is sandwiched between the fixing body 310 and the slide-on element 312 to provide a biasing spring force when the components 302, 310, 312, 316 are mounted in the fitting. The disk spring 316 acting as a spring loading element may alternatively also be noted as a preloading element or a biasing element.

The fixing body 310 is a cone being fixedly connected with the ceramic body 302 and works with respect to the needle body 302 in a form closure way. Since it is made of a ductile material, it will be deformed under pressure so as to provide a clamping force and hence a reliable connection.

FIG. 4 shows an arrangement in which the components of FIG. 3 are mounted in a fitting 402. The fitting 402 is configured for being connectable to the fitting end 306 of the needle body 302 and to components 310, 312. More precisely, the fitting 402 has a reception for receiving a part of the needle body 302, the fixing body 310 and a part of the slide-on element 312. Also the reception is conically tapering in accordance with the conically tapering of the needle body 302, but is tapering with a larger cone angle as compared to the conically tapering of the needle body 302 which contributes to the formation of a pressure-tight sealing between the conically tapering portion of the needle body 302 and the conically tapering recess of the fitting.

For mounting, the integrally formed needle body 302 with the fixing body 310 rigidly attached (for instance soldered) thereto are inserted together into the reception of the fitting 402. The conically tapering portions of the needle body 302 and of the reception of the fitting 402 allow for a centered insertion of the needle body 302 into the reception of the fitting 402. Subsequently, the slide-on element 312 is slid on the needle body 302 from the seat end 308 and is shifted upwardly according to FIG. 4 to abut against a rear surface of the fixing body 310. A screw connection is formed between the external thread 314 of the slide-on element 312 on the one hand and an internal thread 404 provided on an inner surface of the reception of the fitting 402. By taking this measure, the slide-on element 312 exerts a pressing force onto the rear surface of the fixing body 310, which then also presses the needle body 302 towards an abutting wall surface of the fitting 402 according to FIG. 4. Summarizing, the fixing body 310 is pressed on, receives the needle body 302 and presses the needle body 302 against the fitting 402.

More precisely, as can also be taken from the detailed view in FIG. 5, the fitting body 310 presses against a gold plating surface 408 of the fitting 402 to provide for a clamping connection. As an alternative to gold, it is also possible to use for instance a PEEK-coating on element surface 408 to provide for a fluid-tight connection.

As can further be taken from FIG. 4 and FIG. 5, the fitting 402 has a fluid conduit 406 in alignment and fluid communication with the fluid conduit 304 of the needle body 302 when a part of the needle body 302, the fixing body 310 and a part of the slide-on element 312 are mounted in the reception of the fitting 402.

Hence, FIG. 3 to FIG. 5 show a ceramic (zirconium oxide) injection needle 300 for HPLC/UHPLC applications. The ceramic needle 300 has a high inner diameter to outer diameter surface quality and therefore provides advantages in area positions. With the ceramic material, a bio-inert material free of metals may be provided such as $Al_2O_3$, $ZrO_2$ or $ZrO_2$ Yttrium stabilized. Such materials show a low interaction with samples such as biological samples and have a low dispersion connection. With such a ceramic needle 300, it is possible to decrease wear-out in a needle seat combination because of the low friction (smooth surface on tip). Hence, low tightening forces are sufficient for the needle 300. It is also possible to compensate for a coaxial error of connection parts (capillary hole/bore hole). Moreover, a reliable cone/clamp connection is made possible.

More generally, with regard to the functionality of the needle and the fitting connection, a conically shaped ring is pressed in a conically shaped counter ring. The inner diameter of the inner ring is shrinking on a grinding gap on the outer diameter of the ceramic needle. Axial movement is generated by a screw pitch (compare slide-on element), the shrunk ring lifts up the needle into a gold-plated conical hole of the fitting part. A fixed ferrule moves the capillary to the front seal side and presses it on the bottom of the fitting detail. Thus, a pre-stressed chromatographic seal is obtained.

Figure 6:
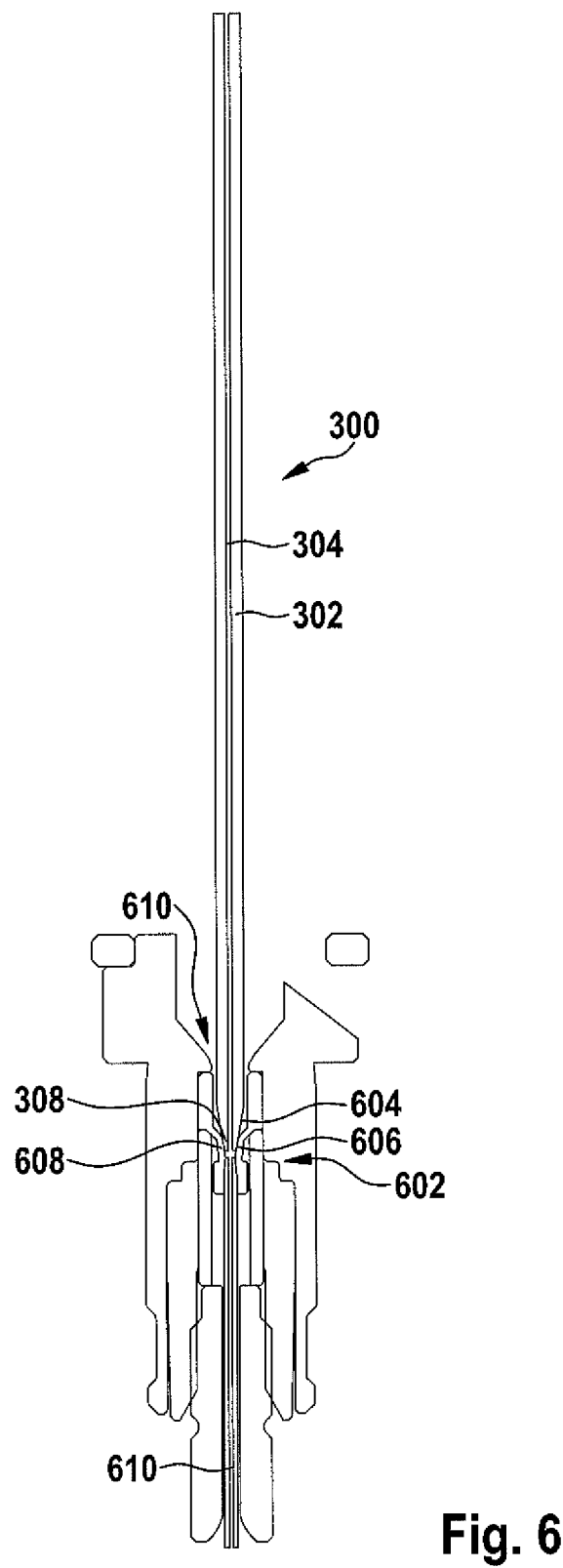
FIG. 6 shows a needle received in a seat of a sample injector according to an embodiment of the present invention.

FIG. 6 shows an arrangement of the needle 300 as shown and described above, but also showing as to how the seat end 308 of the needle 300 is connected to a seat 602.

As described above referring to FIG. 2, the needle 300 is selectively insertable into the seat 602 or is movable out of the seat 602 (for instance to be moved to a vial). For this reason, a conically tapering part 604 of the needle body 302 is configured in accordance with a conically tapering portion 606 of an elastically displaceable element 608 formed in a reception 610 of the seat 602. Therefore, the fluid conduit 304 of the needle body 302 can be brought in alignment with a fluid conduit 610 of the seat 602. A sealed connection is provided between the needle body 302 and the seat 602, as well as a proper alignment between the fluidic conduits 304, 610.

The deformable element 608 can be described as a thin-walled sheath section having a basically conical tapering geometry (and having a kink) and which provides the radially elastic property. This sheath section is made of a hardened steel material, which can be specifically hardened at the surface facing the needle 302.

The elastic element 608 can be elastically widened by the needle 302 and functions as some sort of elastic tension belt around a narrow annular sealing area between the needle 302 and the seat 602. Thus, deformable element 608 is a thin-walled clamping sleeve which elastically snuggles against the contact area of the needle 302, wherein the elastic force is exerted perpendicular to the contact area. Due to the manufacturing process of the needle 302 and the seat 602, profile defects may occur which may result in an interrupted area of a sealing ring, and therefore may result in leakage if the seat 602 does not snugly align to the needle 302. Such profile defects can be balanced in case of a waviness, but cannot be balanced out easily in the form of axial scratches or grooves.

Upon proper alignment between the axis of the needle 302 and the seat 602, the projected sealing area forms an annulus. In case of an axial misalignment between needle 302 and seat 602, the sealing area will become elliptical, i.e. the deformable element 608 needs to be elliptically deformed for sealing.

A closed area of the sealing ring needs to be achieved. In the present scenario of FIG. 6 of a material combination hard/hard (needle 302 of ceramic, deformable element 608 of steel), such a closed annular seal area can be achieved by an elastic snuggling of the deformable element 608.

The thinner the wall of the deformable element 608 is designed and the closer the loads of system pressure and sealing force of the axial needle biasing is designed towards the elastic limit of the material of the deformable element 608, the more balanced is the elastic formation of the deformable element 608.

In view of the foregoing, it is advantageous if the contact surface of the deformable element 608 abutting against the needle 302 is additionally hardened. Apart from the use of extremely strain hardened steels such as Duplex 1.4462 having a proof strength (nominal Rp 0.2) of up to 1400 MPa, this surface can be hardened or hard coated.

With conventional material combinations hard/soft (the soft component being provided by a polymer) of needle/seat arrangements, a sealing effect may be achieved by a plastic deformation, finally resulting in an abrasive wear of the polymeric seat component. Thus, the hard/hard combination of exemplary embodiments of the invention allows to obtain a significantly larger lifetime and may withstand a pressure of 2000 bar or more.

It should be noted that the term "comprising" does not exclude other elements or features and the "a" or "an" does not exclude a plurality. Also elements described in association with different embodiments may be combined. It should also be noted that reference signs in the claims shall not be construed as limiting the scope of the claims.

The invention claimed is:

1. A needle for handling a fluid in an analysis system, the needle comprising:
a needle body made of a ceramic material and having a fluid conduit extending between a fitting end and a seat end, the fitting end being connectable to a fitting and the seat end is configured to be inserted into a seat, wherein the needle body is tapering towards the fitting end;
a fixing body arranged on the needle body next to the fitting end for exerting an axial force when the needle body is connected to the fitting, wherein the fixing body tapers towards the tapering of the needle body;
a slide-on element to be slid over the needle body so as to push the fixing body towards the fitting end; and
a springloading element-arranged over the needle body between the fixing body and the slide-on element.

2. The needle of claim 1, wherein the fixing body is fixedly mounted on the needle body.

3. The needle of claim 1, wherein the fixing body is made of a ductile material, and the needle body is made of a non-ductile material.

4. The needle of claim 1, wherein the needle body is made of one of the group consisting of aluminum oxide, zirconium oxide, and yttrium-stabilized zirconium oxide.

5. The needle of claim 1, wherein the needle body is tapering towards the seat end, wherein the tapering towards the fitting end is steeper than the tapering towards the seat end.

6. The needle of claim 1, wherein the spring-loading, element is a disc spring.

7. A needle assembly comprising the needle of claim 1 and a fitting, wherein the fitting is connected to the fitting end of the needle body.

8. The needle assembly of claim 7, wherein the fitting has a reception for receiving at least a part of the needle body, at least a part of the fixing body and at least a part of the slide-on element, the reception being tapering in accordance with the tapering of the needle body.

9. The needle assembly of claim 8, wherein a cone angle ($\alpha$) of the conically tapering of the needle body is smaller than a cone angle of the conically tapering of the fitting so that a pressure-tight sealing is formed between the conically tapering of the needle body and the conically tapering of the fitting.

10. The needle assembly of claim 8, wherein the fitting has a fluid conduit in fluid communication with the fluid conduit of the needle body when at least a part of the needle body, at least a part of the fixing body and at least a part of the slide-on element are mounted in the reception of the fitting.

11. A needle for handling a fluid in an analysis system, the needle comprising:
a needle body made of a ceramic material and having a fluid conduit extending between a fitting end and a seat end, the fitting end being connectable to a fitting and the seat end is configured to be inserted into a seat, wherein the needle body is tapering towards the fitting end;
a fixing body arranged on the needle body next to the fitting end for exerting an axial force when the needle body is connected to the fitting;
a slide-on element to be slid over the needle body so as to push the fixing body towards the fitting end, wherein the slide-on element has a tubular shape with an inner lumen for receiving the needle body and with an external thread, for cooperation with a needle body fastener of a reception of the fitting; and
a springloading element arranged over the needle body between the fixing body and the slide-on element.

12. The needle of claim 11, wherein the fixing body is fixedly mounted on the needle body.

13. The needle of claim 12, wherein the fixing body is made of a ductile material, and the needle body is made of a non-ductile material.

14. The needle of claim 12, wherein the slide-on element has a tubular shape with an inner lumen for receiving the needle body and with an external thread, for cooperation with a needle body fastener of a reception of the fitting.

15. The needle of claim 12, wherein the needle body is made of one of the group consisting of aluminum oxide, zirconium oxide, and yttrium-stabilized zirconium oxide.

16. The needle of claim 12, wherein the needle body is tapering towards the seat end, wherein the tapering towards the fitting end is steeper than the tapering towards the seat end.

17. The needle of claim 12, wherein the spring-loading element is a disc spring.

18. A needle assembly comprising the needle of claim 12 and a fitting, wherein the fitting is connected to the fitting end of the needle body.

19. The needle assembly of claim 18, wherein the fitting has a reception frit receiving at least a part of the needle body, at least a part of the fixing body and at least a part of the slide-on element, the reception being tapering in accordance with the tapering of the needle body.

20. The needle assembly of claim 19, wherein a cone angle ($\alpha$) of the conically tapering of the needle body is smaller than a cone angle of the conically tapering of the fitting so that a pressure-tight sealing is formed between the conically tapering of the needle body and the conically tapering of the fitting.

21. The needle assembly of claim 19, wherein the fitting has a fluid conduit in fluid communication with the fluid conduit of the needle body when at least a part of the needle body, at least a part of the fixing body and at least a part of the slide-on element are mounted in the reception of the fitting.

* * * * *